United States Patent
Jennings

(10) Patent No.: US 9,028,451 B2
(45) Date of Patent: May 12, 2015

(54) INJECTION DEVICE

(75) Inventor: Douglas Ivan Jennings, Royston (GB)

(73) Assignee: Cilag GmbH International, Landis & Gyrstrasse (CH)

( * ) Notice: Subject to any disclaimer, the term of this patent is extended or adjusted under 35 U.S.C. 154(b) by 1907 days.

(21) Appl. No.: 12/301,480

(22) PCT Filed: May 29, 2007

(86) PCT No.: PCT/GB2007/001969
§ 371 (c)(1),
(2), (4) Date: Jun. 4, 2012

(87) PCT Pub. No.: WO2007/138296
PCT Pub. Date: Dec. 6, 2007

(65) Prior Publication Data
US 2012/0232491 A1     Sep. 13, 2012

(30) Foreign Application Priority Data

Jun. 1, 2006   (GB) .................................. 0610861.7

(51) Int. Cl.
*A61M 5/32*     (2006.01)
*A61M 5/00*     (2006.01)
*A61M 5/20*     (2006.01)

(52) U.S. Cl.
CPC ......... *A61M 5/3202* (2013.01); *Y10T 29/49826* (2015.01); *A61M 5/2033* (2013.01); *A61M 2005/3215* (2013.01)

(58) Field of Classification Search
CPC ............ A61M 5/3202; A61M 5/3204; A61M 5/3213; A61M 2005/3104; A61M 2005/3109; A61M 2005/312; A61M 2005/3215; A61M 39/20; A61B 19/0262
USPC ......................................... 604/192–198, 263
See application file for complete search history.

(56) References Cited

U.S. PATENT DOCUMENTS

| 1,845,036 A | 2/1932 | Busher |
| 2,019,382 A | 10/1935 | Aronson |
| 2,531,267 A | 11/1950 | Harisch |
| 2,764,977 A | 10/1956 | Ferguson |
| 2,828,742 A | 4/1958 | Ashkenaz |
| 3,131,692 A | 5/1964 | Love |

(Continued)

FOREIGN PATENT DOCUMENTS

| CH | 518102 A | 1/1972 |
| CN | 2059579 U | 7/1990 |

(Continued)

OTHER PUBLICATIONS

International Search Report dated Sep. 5, 2005; International Application No. PCT/GB2005/002117.
International Search Report dated May 30, 2006; International Application No. PCT/GB2005/003725.
International Search Report dated Sep. 9, 2005; International Application No. PCT/GB2005/002126.
Australian Search Report dated Dec. 6, 2007; Application No. SG 200608164-0.
International Search Report dated Sep. 5, 2005; International Application No. PCT/GB2005/002131.
Austrian Search Report dated Jan. 22, 2006; Application No. 200608166-5.

(Continued)

*Primary Examiner* — Andrew Gilbert

(57) ABSTRACT

An injection device 110 is described having a housing 112 and a cap 130. The injection device 110 houses a syringe 114 having a needle which is sealed by a boot 118. The cap 130 is arranged so that the boot 118 can be connected to the cap 130 while exerting a minimal force on the syringe, but cannot be removed from the cap 130 without applying a significantly greater force to the syringe. The housing 112 and cap 130 are arranged so that upon removal of the cap 130 from the housing 112, the boot 118 is removed from the syringe 114.

26 Claims, 4 Drawing Sheets

(56) References Cited

U.S. PATENT DOCUMENTS

| | | |
|---|---|---|
| 3,320,955 A | 5/1967 | Sarnoff |
| 3,329,146 A | 7/1967 | Waldman |
| 3,543,603 A | 12/1970 | Gley |
| 3,656,472 A | 4/1972 | Moura |
| 3,702,608 A | 11/1972 | Tibbs |
| 3,742,948 A | 7/1973 | Post et al. |
| 3,797,488 A | 3/1974 | Hurschman et al. |
| 3,797,489 A | 3/1974 | Sarnoff |
| 3,880,163 A | 4/1975 | Ritterskamp |
| 3,976,069 A | 8/1976 | Ong |
| 4,165,739 A | 8/1979 | Doherty et al. |
| 4,180,070 A | 12/1979 | Genese |
| 4,185,628 A | 1/1980 | Kopfer |
| 4,194,505 A | 3/1980 | Schmitz |
| 4,222,380 A | 9/1980 | Terayama |
| 4,231,368 A | 11/1980 | Becker |
| 4,236,516 A | 12/1980 | Nilson |
| 4,299,238 A | 11/1981 | Baidwan et al. |
| 4,333,459 A | 6/1982 | Becker |
| 4,378,015 A | 3/1983 | Wardlaw |
| 4,394,863 A | 7/1983 | Bartner |
| 4,403,989 A | 9/1983 | Christensen et al. |
| 4,407,283 A | 10/1983 | Reynolds |
| 4,425,120 A | 1/1984 | Sampson et al. |
| 4,430,082 A | 2/1984 | Schwabacher |
| 4,521,237 A | 6/1985 | Logothetis |
| 4,561,856 A | 12/1985 | Cochran et al. |
| 4,636,201 A | 1/1987 | Ambrose et al. |
| 4,639,250 A | 1/1987 | Rycroft |
| 4,642,099 A | 2/1987 | Phillips et al. |
| 4,676,530 A | 6/1987 | Nordgren et al. |
| 4,744,786 A | 5/1988 | Hooven et al. |
| 4,787,891 A | 11/1988 | Levin et al. |
| 4,874,383 A | 10/1989 | McNaughton |
| 4,874,384 A | 10/1989 | Nunez |
| 4,929,232 A | 5/1990 | Sweeney et al. |
| 4,969,870 A | 11/1990 | Kramer et al. |
| 4,988,339 A | 1/1991 | Vadher |
| 5,009,646 A | 4/1991 | Sudo et al. |
| 5,026,349 A | 6/1991 | Schmitz et al. |
| 5,057,079 A | 10/1991 | Tiemann et al. |
| 5,092,842 A | 3/1992 | Bechtold et al. |
| 5,098,400 A | 3/1992 | Crouse et al. |
| 5,112,119 A | 5/1992 | Cooke et al. |
| 5,114,406 A | 5/1992 | Gabriel et al. |
| 5,122,119 A | 6/1992 | Lucas |
| 5,137,516 A | 8/1992 | Rand et al. |
| 5,141,496 A | 8/1992 | Dalto et al. |
| 5,147,325 A | 9/1992 | Mitchell et al. |
| 5,156,599 A | 10/1992 | Ranford et al. |
| 5,176,643 A | 1/1993 | Kramer et al. |
| 5,190,526 A | 3/1993 | Murray et al. |
| 5,242,416 A | 9/1993 | Hutson |
| 5,250,026 A | 10/1993 | Ehrlich et al. |
| 5,250,037 A | 10/1993 | Bitdinger |
| 5,263,933 A | 11/1993 | Novacek et al. |
| 5,267,963 A | 12/1993 | Bachynsky |
| 5,271,744 A | 12/1993 | Kramer et al. |
| 5,295,965 A | 3/1994 | Wilmot |
| 5,300,030 A | 4/1994 | Crossman et al. |
| 5,312,364 A | 5/1994 | Jacobs |
| 5,330,081 A | 7/1994 | Davenport |
| 5,330,430 A | 7/1994 | Sullivan |
| 5,358,489 A | 10/1994 | Wyrick |
| 5,364,369 A | 11/1994 | Reynolds |
| 5,368,577 A | 11/1994 | Teoh et al. |
| 5,372,586 A | 12/1994 | Haber et al. |
| 5,391,151 A | 2/1995 | Wilmot |
| 5,405,362 A | 4/1995 | Kramer et al. |
| 5,411,488 A | 5/1995 | Pagay et al. |
| 5,425,715 A | 6/1995 | Dalling et al. |
| 5,451,210 A | 9/1995 | Kramer et al. |
| 5,478,316 A | 12/1995 | Bitdinger et al. |
| 5,480,387 A | 1/1996 | Gabriel et al. |
| 5,487,732 A | 1/1996 | Jeffrey |
| 5,489,256 A | 2/1996 | Adair |
| 5,503,627 A | 4/1996 | McKinnon et al. |
| 5,514,097 A | 5/1996 | Knauer |
| 5,520,653 A | 5/1996 | Reilly et al. |
| 5,540,660 A | 7/1996 | Jenson et al. |
| 5,540,666 A | 7/1996 | Barta et al. |
| 5,540,709 A | 7/1996 | Ramel et al. |
| 5,567,160 A | 10/1996 | Massino |
| 5,569,191 A | 10/1996 | Meyer |
| 5,569,192 A | 10/1996 | van der Wal |
| 5,575,777 A | 11/1996 | Cover et al. |
| 5,599,302 A | 2/1997 | Lilley et al. |
| 5,599,309 A | 2/1997 | Marshall et al. |
| 5,607,395 A | 3/1997 | Ragsdale et al. |
| 5,609,577 A | 3/1997 | Haber et al. |
| 5,609,584 A | 3/1997 | Gettig et al. |
| 5,611,785 A | 3/1997 | Mito et al. |
| 5,637,094 A | 6/1997 | Stewart, Jr. et al. |
| 5,645,536 A | 7/1997 | Whisson |
| 5,647,845 A | 7/1997 | Haber et al. |
| 5,649,912 A | 7/1997 | Peterson |
| 5,658,259 A * | 8/1997 | Pearson et al. ............. 604/232 |
| 5,665,071 A | 9/1997 | Wyrick |
| 5,681,291 A | 10/1997 | Galli |
| 5,697,908 A | 12/1997 | Imbert |
| 5,702,367 A | 12/1997 | Cover et al. |
| 5,704,911 A | 1/1998 | Parsons et al. |
| 5,709,662 A * | 1/1998 | Olive et al. ............. 604/135 |
| 5,713,866 A | 2/1998 | Wilmot |
| 5,748,316 A | 5/1998 | Wakabayashi et al. |
| 5,779,668 A | 7/1998 | Grabenkort |
| 5,779,677 A | 7/1998 | Frezza |
| 5,807,334 A | 9/1998 | Hodosh et al. |
| 5,817,058 A | 10/1998 | Shaw |
| 5,827,262 A | 10/1998 | Neftel et al. |
| 5,843,036 A * | 12/1998 | Olive et al. ............. 604/136 |
| 5,855,839 A | 1/1999 | Brunel |
| 5,865,795 A | 2/1999 | Schiff et al. |
| 5,865,804 A | 2/1999 | Bachynsky |
| 5,868,711 A | 2/1999 | Kramer et al. |
| 5,879,327 A | 3/1999 | Moreau DeFarges et al. |
| 5,913,843 A | 6/1999 | Jentzen |
| 5,928,205 A * | 7/1999 | Marshall ............. 604/263 |
| 5,954,738 A | 9/1999 | LeVaughn et al. |
| 5,957,897 A | 9/1999 | Jeffrey |
| 5,960,797 A | 10/1999 | Kramer et al. |
| 5,997,513 A | 12/1999 | Smith et al. |
| 6,007,515 A | 12/1999 | Epstein et al. |
| 6,015,438 A | 1/2000 | Shaw |
| 6,017,330 A | 1/2000 | Hitchins et al. |
| 6,036,675 A | 3/2000 | Thorne et al. |
| 6,045,534 A | 4/2000 | Jacobsen et al. |
| 6,068,614 A | 5/2000 | Kimber et al. |
| 6,077,247 A | 6/2000 | Marshall et al. |
| 6,083,197 A | 7/2000 | Umbaugh |
| 6,086,562 A | 7/2000 | Jacobsen et al. |
| 6,090,070 A | 7/2000 | Hager et al. |
| 6,090,078 A | 7/2000 | Erskine |
| 6,090,897 A | 7/2000 | Akasaki et al. |
| 6,099,503 A | 8/2000 | Stradella |
| 6,099,504 A | 8/2000 | Gross |
| 6,123,684 A | 9/2000 | Deboer et al. |
| 6,139,534 A | 10/2000 | Niedospial, Jr. et al. |
| 6,159,161 A | 12/2000 | Hodosh |
| 6,159,181 A | 12/2000 | Crossman et al. |
| 6,159,184 A | 12/2000 | Perez et al. |
| 6,162,199 A | 12/2000 | Geringer |
| 6,171,276 B1 | 1/2001 | Lippe et al. |
| 6,179,812 B1 | 1/2001 | Botich et al. |
| 6,186,980 B1 * | 2/2001 | Brunel ............. 604/110 |
| 6,190,363 B1 | 2/2001 | Gabbard et al. |
| 6,193,696 B1 | 2/2001 | Jansen et al. |
| 6,203,530 B1 | 3/2001 | Stewart, Sr. |
| 6,209,738 B1 | 4/2001 | Jansen et al. |
| 6,221,044 B1 | 4/2001 | Grecco |
| 6,258,068 B1 | 7/2001 | Kirchhofer et al. |
| 6,270,479 B1 | 8/2001 | Bergens et al. |
| 6,280,421 B1 | 8/2001 | Kirchhofer et al. |
| 6,290,683 B1 | 9/2001 | Erez et al. |

(56) References Cited

U.S. PATENT DOCUMENTS

| | | |
|---|---|---|
| 6,293,925 B1 | 9/2001 | Safabash et al. |
| 6,317,939 B1 | 11/2001 | Malin |
| 6,330,960 B1 | 12/2001 | Faughey et al. |
| 6,332,875 B2 | 12/2001 | Inkpen et al. |
| 6,371,939 B2 | 4/2002 | Bergens et al. |
| 6,371,959 B1 | 4/2002 | Trice |
| 6,387,078 B1 | 5/2002 | Gillespie, III |
| 6,391,003 B1 | 5/2002 | Lesch, Jr. |
| 6,419,658 B1 | 7/2002 | Restelli et al. |
| 6,428,528 B2 | 8/2002 | Sadowski et al. |
| 6,447,480 B1 | 9/2002 | Brunel |
| 6,454,743 B1 | 9/2002 | Weber |
| 6,454,746 B1 | 9/2002 | Bydion et al. |
| 6,461,333 B1 | 10/2002 | Frezza |
| 6,491,667 B1 | 12/2002 | Keane et al. |
| 6,517,517 B1 | 2/2003 | Farrugia et al. |
| 6,537,252 B1 | 3/2003 | Hansen |
| 6,544,234 B1 | 4/2003 | Gabriel |
| 6,565,540 B1 | 5/2003 | Perouse et al. |
| 6,565,553 B2 | 5/2003 | Sadowski et al. |
| 6,569,115 B1 | 5/2003 | Barker et al. |
| 6,569,123 B2 | 5/2003 | Alchas et al. |
| 6,569,124 B1 | 5/2003 | Perouse |
| 6,572,581 B1 | 6/2003 | Landau |
| 6,575,939 B1 * | 6/2003 | Brunel .......................... 604/187 |
| 6,585,702 B1 * | 7/2003 | Brunel .......................... 604/263 |
| 6,589,210 B1 | 7/2003 | Rolfe |
| 6,595,957 B1 | 7/2003 | Griffiths et al. |
| 6,595,962 B1 | 7/2003 | Perthu |
| 6,599,272 B1 | 7/2003 | Hjertman et al. |
| 6,607,508 B2 | 8/2003 | Knauer |
| 6,607,510 B2 | 8/2003 | Landau |
| 6,613,022 B1 | 9/2003 | Doyle |
| 6,620,137 B2 | 9/2003 | Kirchhofer et al. |
| 6,638,256 B2 | 10/2003 | Jansen et al. |
| 6,641,554 B2 | 11/2003 | Landau |
| 6,641,560 B1 | 11/2003 | Bechtold et al. |
| 6,641,565 B1 | 11/2003 | Lavi et al. |
| 6,645,170 B2 | 11/2003 | Landua |
| 6,645,181 B1 | 11/2003 | Lavi et al. |
| 6,648,835 B1 | 11/2003 | Shemesh |
| 6,648,850 B2 | 11/2003 | Landau |
| 6,656,163 B1 | 12/2003 | Marshall et al. |
| 6,673,049 B2 | 1/2004 | Hommann et al. |
| 6,676,630 B2 | 1/2004 | Landau et al. |
| 6,689,093 B2 | 2/2004 | Landau et al. |
| 6,692,469 B1 | 2/2004 | Weekes et al. |
| 6,699,220 B2 | 3/2004 | Rolfe |
| 6,740,062 B2 | 5/2004 | Hjertman |
| 6,743,199 B2 | 6/2004 | Shue et al. |
| 6,743,203 B1 | 6/2004 | Pickhard et al. |
| 6,746,429 B2 | 6/2004 | Sadowski et al. |
| 6,746,438 B1 | 6/2004 | Arnissolle |
| 6,767,336 B1 | 7/2004 | Kaplan |
| 6,770,056 B2 | 8/2004 | Price et al. |
| 6,776,777 B2 | 8/2004 | Barrelle |
| 6,783,509 B1 | 8/2004 | Landau et al. |
| 6,793,161 B1 | 9/2004 | Fujita et al. |
| 6,796,967 B2 | 9/2004 | Jensen |
| 6,811,548 B2 | 11/2004 | Jeffrey |
| 6,846,303 B2 | 1/2005 | Eakins et al. |
| 6,875,205 B2 | 4/2005 | Leinsing |
| 6,890,319 B1 | 5/2005 | Crocker |
| 6,899,698 B2 | 5/2005 | Sams |
| 6,902,543 B1 | 6/2005 | Cherif-Cheikh et al. |
| 6,932,793 B1 | 8/2005 | Marshall et al. |
| 6,939,319 B1 | 9/2005 | Anstead et al. |
| 6,979,316 B1 | 12/2005 | Rubin et al. |
| 7,066,907 B2 | 6/2006 | Crossman et al. |
| 7,097,071 B2 | 8/2006 | Anderson et al. |
| 7,097,634 B2 | 8/2006 | Gilbert |
| 7,118,553 B2 | 10/2006 | Scherer |
| 7,156,823 B2 | 1/2007 | Landau et al. |
| 7,160,913 B2 | 1/2007 | Schneider |
| 7,294,122 B2 | 11/2007 | Kubo et al. |
| 7,354,427 B2 | 4/2008 | Fangrow |
| RE40,428 E | 7/2008 | Keane et al. |
| 7,442,185 B2 | 10/2008 | Amark et al. |
| 7,470,258 B2 | 12/2008 | Barker et al. |
| 7,507,227 B2 | 3/2009 | Fangrow |
| 7,510,547 B2 | 3/2009 | Fangrow |
| 7,510,548 B2 | 3/2009 | Fangrow |
| 7,513,895 B2 | 4/2009 | Fangrow |
| 7,534,238 B2 | 5/2009 | Fangrow |
| 7,547,300 B2 | 6/2009 | Fangrow |
| 7,569,043 B2 | 8/2009 | Fangrow |
| 7,618,396 B2 | 11/2009 | Slate et al. |
| 7,645,271 B2 | 1/2010 | Fangrow |
| 7,654,995 B2 | 2/2010 | Warren et al. |
| 7,658,733 B2 | 2/2010 | Fangrow |
| 7,678,333 B2 | 3/2010 | Reynolds et al. |
| 7,682,345 B2 | 3/2010 | Savage |
| 7,717,879 B2 | 5/2010 | Mansouri |
| 7,744,561 B2 | 6/2010 | Stamp |
| 7,759,654 B2 | 7/2010 | Yan et al. |
| 7,794,434 B2 | 9/2010 | Mounce et al. |
| 7,799,009 B2 | 9/2010 | Niedospial, Jr. et al. |
| 7,811,262 B2 | 10/2010 | Moberg et al. |
| 7,828,764 B2 | 11/2010 | Moberg et al. |
| 7,879,010 B2 | 2/2011 | Hunn et al. |
| 7,883,499 B2 | 2/2011 | Fangrow |
| 7,959,715 B2 | 6/2011 | Kavazov et al. |
| 7,972,321 B2 | 7/2011 | Fangrow |
| 7,976,499 B2 | 7/2011 | Grunhut et al. |
| 8,100,154 B2 | 1/2012 | Reynolds et al. |
| 8,177,768 B2 | 5/2012 | Leinsing |
| 8,313,463 B2 | 11/2012 | Barrow-Williams et al. |
| 8,409,138 B2 | 4/2013 | James et al. |
| 8,491,530 B2 | 7/2013 | Maritan |
| 8,696,628 B2 | 4/2014 | Grunhut |
| 2001/0005781 A1 | 6/2001 | Bergens et al. |
| 2001/0021828 A1 | 9/2001 | Fischer et al. |
| 2001/0037087 A1 | 11/2001 | Knauer |
| 2001/0037089 A1 | 11/2001 | Domici, Jr. |
| 2001/0049496 A1 | 12/2001 | Kirchhofer et al. |
| 2001/0051789 A1 | 12/2001 | Parsons |
| 2002/0032412 A1 | 3/2002 | Riemelmoser |
| 2002/0072709 A1 | 6/2002 | Sadowski et al. |
| 2002/0095120 A1 | 7/2002 | Larsen et al. |
| 2002/0151839 A1 | 10/2002 | Landau |
| 2002/0161334 A1 | 10/2002 | Castellano et al. |
| 2002/0165500 A1 | 11/2002 | Bechtold et al. |
| 2002/0173752 A1 | 11/2002 | Polzin |
| 2002/0183690 A1 | 12/2002 | Arnisolle |
| 2003/0036679 A1 | 2/2003 | Kortenbach |
| 2003/0036725 A1 | 2/2003 | Lavi et al. |
| 2003/0050609 A1 | 3/2003 | Sams |
| 2003/0060773 A1 | 3/2003 | Nguyen |
| 2003/0065286 A1 | 4/2003 | Landau |
| 2003/0078546 A1 | 4/2003 | Jensen |
| 2003/0088207 A1 | 5/2003 | Rogatchev et al. |
| 2003/0088216 A1 | 5/2003 | Py |
| 2003/0093030 A1 | 5/2003 | Landau |
| 2003/0093035 A1 | 5/2003 | Mohammed |
| 2003/0093036 A1 | 5/2003 | Crossman et al. |
| 2003/0105430 A1 | 6/2003 | Lavi et al. |
| 2003/0109833 A1 | 6/2003 | Sahpe |
| 2003/0120212 A1 | 6/2003 | Dedig et al. |
| 2003/0120222 A1 | 6/2003 | Vaillancourt |
| 2003/0121815 A1 | 7/2003 | Bergeron et al. |
| 2003/0135157 A1 | 7/2003 | Saulenas et al. |
| 2003/0181859 A1 | 9/2003 | Brunel |
| 2003/0184973 A1 | 10/2003 | Nagata et al. |
| 2003/0196928 A1 | 10/2003 | Parsons |
| 2003/0199814 A1 | 10/2003 | Parsons et al. |
| 2003/0208164 A1 | 11/2003 | Botich et al. |
| 2003/0212362 A1 | 11/2003 | Roser |
| 2003/0212370 A1 | 11/2003 | Barrelle |
| 2003/0212380 A1 | 11/2003 | Barrelle |
| 2003/0225368 A1 | 12/2003 | Landau et al. |
| 2003/0229308 A1 | 12/2003 | Tsals et al. |
| 2003/0233070 A1 | 12/2003 | De La serna et al. |
| 2003/0236502 A1 | 12/2003 | De La Serna et al. |
| 2003/0236504 A1 | 12/2003 | Chen |

(56) References Cited

U.S. PATENT DOCUMENTS

| | | |
|---|---|---|
| 2004/0002684 A1 | 1/2004 | Lopez |
| 2004/0015134 A1 | 1/2004 | Lavi et al. |
| 2004/0019326 A1 | 1/2004 | Gilbert et al. |
| 2004/0024367 A1 | 2/2004 | Gilbert |
| 2004/0039336 A1 | 2/2004 | Amark et al. |
| 2004/0039366 A1 | 2/2004 | MacLeod |
| 2004/0069044 A1 | 4/2004 | Lavi et al. |
| 2004/0087897 A1 | 5/2004 | Hjertman |
| 2004/0102740 A1 | 5/2004 | Meloul |
| 2004/0111054 A1 | 6/2004 | Landau et al. |
| 2004/0111057 A1 | 6/2004 | Wilkinson |
| 2004/0133159 A1 | 7/2004 | Haider et al. |
| 2004/0138618 A1 | 7/2004 | Mazzoni |
| 2004/0143224 A1 | 7/2004 | Field et al. |
| 2004/0153033 A1 | 8/2004 | Mazzoni |
| 2004/0225262 A1 | 11/2004 | Fathallah et al. |
| 2004/0243065 A1 | 12/2004 | McConnell et al. |
| 2005/0011780 A1 | 1/2005 | Simon et al. |
| 2005/0020979 A1 | 1/2005 | Westbye et al. |
| 2005/0020980 A1 | 1/2005 | Inoue et al. |
| 2005/0027255 A1 | 2/2005 | Lavi et al. |
| 2005/0033234 A1 | 2/2005 | Sadowski et al. |
| 2005/0035029 A1 | 2/2005 | Grob |
| 2005/0040716 A1 | 2/2005 | Schmid et al. |
| 2005/0049550 A1 | 3/2005 | Kirchhofer et al. |
| 2005/0049561 A1 | 3/2005 | Hommann et al. |
| 2005/0075608 A1 | 4/2005 | Holdgate et al. |
| 2005/0085776 A1 | 4/2005 | Hommann et al. |
| 2005/0090782 A1 | 4/2005 | Marshall et al. |
| 2005/0097238 A1 | 5/2005 | Oomori et al. |
| 2005/0101919 A1 | 5/2005 | Brunnberg |
| 2005/0113747 A1 | 5/2005 | Moir |
| 2005/0124940 A1 | 6/2005 | Martin et al. |
| 2005/0125019 A1 | 6/2005 | Kudna et al. |
| 2005/0137523 A1 | 6/2005 | Wyatt et al. |
| 2005/0165360 A1* | 7/2005 | Stamp ......................... 604/187 |
| 2005/0168855 A1 | 8/2005 | Fanelli et al. |
| 2005/0203466 A1 | 9/2005 | Hommann et al. |
| 2005/0209554 A1 | 9/2005 | Landau |
| 2005/0215941 A1 | 9/2005 | Bernard et al. |
| 2005/0215951 A1 | 9/2005 | Saulenas et al. |
| 2005/0222539 A1 | 10/2005 | Gonzales et al. |
| 2005/0261633 A1 | 11/2005 | Khalaj |
| 2005/0261634 A1 | 11/2005 | Karlsson |
| 2005/0267403 A1 | 12/2005 | Landau et al. |
| 2005/0273054 A1 | 12/2005 | Asch |
| 2005/0273055 A1 | 12/2005 | Harrison et al. |
| 2005/0277885 A1 | 12/2005 | Scherer |
| 2005/0277886 A1 | 12/2005 | Hommann et al. |
| 2005/0277896 A1 | 12/2005 | Messerli et al. |
| 2005/0288633 A1 | 12/2005 | Jeffrey |
| 2006/0016835 A1 | 1/2006 | Perry |
| 2006/0030819 A1 | 2/2006 | Young et al. |
| 2006/0036216 A1 | 2/2006 | Rimlinger et al. |
| 2006/0036217 A1 | 2/2006 | Doyle |
| 2006/0069345 A1 | 3/2006 | Anderson et al. |
| 2006/0069348 A1 | 3/2006 | Parker et al. |
| 2006/0069350 A1 | 3/2006 | Buenger et al. |
| 2006/0079834 A1 | 4/2006 | Tennican et al. |
| 2006/0100588 A1 | 5/2006 | Brunnberg et al. |
| 2006/0106295 A1 | 5/2006 | Jais et al. |
| 2006/0161111 A1 | 7/2006 | Potter et al. |
| 2006/0178631 A1 | 8/2006 | Gillespie et al. |
| 2006/0178642 A1 | 8/2006 | Gillespie et al. |
| 2006/0184119 A1 | 8/2006 | Remde et al. |
| 2006/0184137 A1 | 8/2006 | Reynolds |
| 2006/0189938 A1 | 8/2006 | Hommann et al. |
| 2006/0200093 A1 | 9/2006 | Lopez |
| 2006/0206060 A1 | 9/2006 | Lopez |
| 2006/0224124 A1 | 10/2006 | Scherer |
| 2006/0229572 A1 | 10/2006 | Lopez |
| 2006/0258986 A1 | 11/2006 | Hunter et al. |
| 2006/0258990 A1 | 11/2006 | Weber |
| 2006/0270986 A1 | 11/2006 | Hommann et al. |
| 2007/0027430 A1 | 2/2007 | Hommann |
| 2007/0066939 A1 | 3/2007 | Krulevitch et al. |
| 2007/0078382 A1 | 4/2007 | Hommann et al. |
| 2007/0118094 A1 | 5/2007 | Bingham et al. |
| 2007/0142787 A1 | 6/2007 | Scherer |
| 2007/0156091 A1 | 7/2007 | Fathallah et al. |
| 2007/0156112 A1 | 7/2007 | Walsh |
| 2007/0208296 A1 | 9/2007 | Paproski et al. |
| 2008/0033395 A1 | 2/2008 | Alchas |
| 2008/0154192 A1* | 6/2008 | Schraga ...................... 604/110 |
| 2008/0172024 A1 | 7/2008 | Yow |
| 2008/0213590 A1 | 9/2008 | Greiner et al. |
| 2008/0269680 A1 | 10/2008 | Ibranyan et al. |
| 2008/0306443 A1 | 12/2008 | Neer et al. |
| 2008/0312592 A1* | 12/2008 | Barrow-Williams et al. 604/136 |
| 2008/0312602 A1 | 12/2008 | Barrow-Williams et al. |
| 2008/0312606 A1 | 12/2008 | Harrison et al. |
| 2009/0036764 A1 | 2/2009 | Rivas et al. |
| 2009/0054849 A1 | 2/2009 | Burnell et al. |
| 2009/0088688 A1 | 4/2009 | Timothy Donald et al. |
| 2009/0209554 A1 | 8/2009 | Boyd et al. |
| 2009/0234297 A1 | 9/2009 | Jennings |
| 2010/0016793 A1 | 1/2010 | Jennings et al. |
| 2010/0036319 A1 | 2/2010 | Drake et al. |
| 2011/0092954 A1 | 4/2011 | Jennings |
| 2011/0098647 A1 | 4/2011 | Jennings |
| 2011/0098655 A1 | 4/2011 | Jennings et al. |
| 2011/0130743 A1 | 6/2011 | Jennings et al. |
| 2011/0282278 A1* | 11/2011 | Stamp et al. ................ 604/110 |
| 2012/0232491 A1 | 9/2012 | Jennings |
| 2012/0323177 A1 | 12/2012 | Adams et al. |
| 2013/0096512 A1 | 4/2013 | Ekman et al. |
| 2013/0267898 A1 | 10/2013 | Hourmand et al. |
| 2013/0317446 A1 | 11/2013 | Hourmand et al. |
| 2013/0331794 A1 | 12/2013 | Ekman et al. |
| 2013/0338601 A1 | 12/2013 | Cowe |
| 2013/0345643 A1 | 12/2013 | Hourmand et al. |

FOREIGN PATENT DOCUMENTS

| | | |
|---|---|---|
| CN | 1190599 A | 8/1998 |
| CN | 1420794 A | 5/2003 |
| CN | 1541121 A | 10/2004 |
| CN | 1550240 A | 12/2004 |
| CN | 101014379 A | 8/2007 |
| CN | 101068585 A | 11/2007 |
| DE | 902776 C | 1/1954 |
| DE | 229932 A1 | 11/1985 |
| DE | 3604826 A1 | 10/1986 |
| DE | 4428467 A1 | 2/1996 |
| DE | 29513214 U1 | 1/1997 |
| DE | 19603707 A1 | 8/1997 |
| DE | 69506521 T2 | 6/1999 |
| DE | 10137962 A1 | 2/2003 |
| DE | 10207276 A1 | 9/2003 |
| DE | 20311996 U1 | 10/2003 |
| EP | 0111724 B1 | 11/1983 |
| EP | 0096314 A2 | 12/1983 |
| EP | 0144625 A2 | 6/1985 |
| EP | 0240787 A2 | 3/1987 |
| EP | 0515473 B1 | 12/1992 |
| EP | 0518416 A1 | 12/1992 |
| EP | 0331452 A2 | 8/1993 |
| EP | 0585626 A1 | 3/1994 |
| EP | 0389938 B1 | 5/1994 |
| EP | 0516473 B1 | 2/1996 |
| EP | 0482677 B1 | 4/1998 |
| EP | 0602883 B1 | 7/1998 |
| EP | 0857491 A1 | 8/1998 |
| EP | 0824922 B1 | 4/2002 |
| EP | 1260241 A1 | 11/2002 |
| EP | 0824923 B1 | 7/2003 |
| EP | 1228777 B1 | 10/2003 |
| EP | 0991441 B1 | 12/2003 |
| EP | 1166809 B1 | 3/2004 |
| EP | 0666084 B1 | 4/2004 |
| EP | 0941133 B1 | 4/2004 |
| EP | 1124601 B1 | 12/2004 |
| EP | 1364667 B1 | 4/2005 |
| EP | 1208858 B1 | 6/2006 |

(56) References Cited

FOREIGN PATENT DOCUMENTS

| | | |
|---|---|---|
| EP | 1755710 A1 | 2/2007 |
| EP | 1586341 B1 | 1/2008 |
| EP | 2023980 A1 | 2/2009 |
| EP | 2129414 A1 | 12/2009 |
| EP | 1755706 B1 | 3/2010 |
| EP | 1928523 B1 | 7/2010 |
| EP | 1518575 B1 | 11/2010 |
| EP | 1932558 B1 | 6/2011 |
| EP | 2468330 A1 | 6/2012 |
| FR | 1014881 A | 8/1952 |
| FR | 1169935 A | 1/1959 |
| FR | 1538565 A | 9/1968 |
| FR | 2506161 A1 | 11/1982 |
| FR | 2629706 A | 10/1989 |
| FR | 2654938 A1 | 5/1991 |
| FR | 2665079 A1 | 1/1992 |
| FR | 2717086 A1 | 9/1995 |
| FR | 2741810 A1 | 6/1997 |
| FR | 2805868 A1 | 9/2001 |
| FR | 2830765 A1 | 4/2003 |
| FR | 2861310 A1 | 4/2005 |
| GB | 143084 | 5/1920 |
| GB | 0412054 | 6/1934 |
| GB | 728248 | 4/1955 |
| GB | 909898 | 11/1962 |
| GB | 1263355 | 2/1972 |
| GB | 1311937 A | 3/1973 |
| GB | 1514725 A | 6/1978 |
| GB | 2388033 A | 11/2003 |
| GB | 2396298 A | 6/2004 |
| GB | 2396816 A | 7/2004 |
| GB | 2397767 A | 8/2004 |
| GB | 2404338 A | 2/2005 |
| GB | 2414398 A | 11/2005 |
| GB | 2414399 A | 11/2005 |
| GB | 2414400 A | 11/2005 |
| GB | 2414401 A | 11/2005 |
| GB | 2414402 A | 11/2005 |
| GB | 2414403 A | 11/2005 |
| GB | 2424835 A | 10/2006 |
| GB | 2424836 A | 10/2006 |
| GB | 2424837 A | 10/2006 |
| GB | 2424838 A | 10/2006 |
| GB | 2425062 A | 10/2006 |
| GB | 2433035 A | 6/2007 |
| GB | 2437922 A | 11/2007 |
| GB | 2438591 A | 12/2007 |
| GB | 2443606 A | 5/2008 |
| GB | 2445090 A | 6/2008 |
| GB | 2446778 A | 8/2008 |
| GB | 2451663 A | 2/2009 |
| GB | 2451665 A | 2/2009 |
| GB | 2452286 A | 3/2009 |
| JP | 59-115053 A | 7/1984 |
| JP | 2-185261 A | 7/1990 |
| JP | 2-502971 T | 9/1990 |
| JP | 02-299660 A | 12/1990 |
| JP | H02-299660 A | 12/1990 |
| JP | 11-501549 T | 2/1992 |
| JP | 5-161712 A | 6/1993 |
| JP | 6-209996 A | 8/1994 |
| JP | 6-508773 T | 10/1994 |
| JP | 6-327770 A | 11/1994 |
| JP | 07-116224 A | 5/1995 |
| JP | H07-116224 A | 5/1995 |
| JP | 7-213610 A | 8/1995 |
| JP | 7-222799 A | 8/1995 |
| JP | 8-502180 T | 3/1996 |
| JP | 8-504354 T | 5/1996 |
| JP | 9-225029 A | 9/1997 |
| JP | 10-504474 T | 5/1998 |
| JP | 10-507935 A | 8/1998 |
| JP | 11-503637 T | 3/1999 |
| JP | 11-504536 T | 4/1999 |
| JP | 11-164887 T | 6/1999 |
| JP | 11-512332 T | 10/1999 |
| JP | 2000-126293 A | 5/2000 |
| JP | 2000-510021 T | 8/2000 |
| JP | 2001-046498 A | 2/2001 |
| JP | 2001-212237 A | 8/2001 |
| JP | 2002-500933 T | 1/2002 |
| JP | 2002-502296 T | 1/2002 |
| JP | 2002-095749 A | 4/2002 |
| JP | 2002-513547 T | 5/2002 |
| JP | 2002-526175 A | 8/2002 |
| JP | 2002-528182 T | 9/2002 |
| JP | 2002-532161 T | 10/2002 |
| JP | 2003-511105 T | 3/2003 |
| JP | 2003-532500 T | 11/2003 |
| JP | 2003-533288 A | 11/2003 |
| JP | 2004-533282 T | 11/2004 |
| JP | 2004-537376 T | 12/2004 |
| JP | 2005-508214 A | 3/2005 |
| JP | 2005-177503 A | 7/2005 |
| JP | 2004-33737 A | 8/2005 |
| JP | 2006-223858 A | 8/2006 |
| JP | 2008-284177 A | 11/2008 |
| NZ | 335985 A | 4/2001 |
| NZ | 573171 A | 11/2010 |
| NZ | 573350 A | 12/2010 |
| WO | WO 88/10129 A1 | 12/1988 |
| WO | WO 98/10129 A1 | 12/1988 |
| WO | WO 92/19296 A | 11/1992 |
| WO | WO 93/02186 A1 | 2/1993 |
| WO | WO 93/21986 A2 | 11/1993 |
| WO | WO 93/23098 A1 | 11/1993 |
| WO | WO 94/04207 A1 | 3/1994 |
| WO | WO 94/07554 A1 | 4/1994 |
| WO | WO 94/11041 | 5/1994 |
| WO | WO 94/13342 A1 | 6/1994 |
| WO | WO 94/21316 A1 | 9/1994 |
| WO | WO 94/22511 A1 | 10/1994 |
| WO | WO 95/04562 A1 | 2/1995 |
| WO | WO 95/29720 A1 | 11/1995 |
| WO | WO 95/31235 A1 | 11/1995 |
| WO | WO 95/35126 A1 | 11/1995 |
| WO | WO 95/35126 A1 | 12/1995 |
| WO | 96/30065 A1 | 10/1996 |
| WO | WO 96/30065 A1 | 10/1996 |
| WO | WO 97/10865 A1 | 3/1997 |
| WO | WO 97/13538 A1 | 4/1997 |
| WO | WO 97/48430 A1 | 12/1997 |
| WO | WO 98/11927 A1 | 3/1998 |
| WO | WO 99/03529 A2 | 1/1999 |
| WO | WO 99/10030 A2 | 3/1999 |
| WO | WO 99/22789 A1 | 5/1999 |
| WO | WO 99/37343 A | 7/1999 |
| WO | WO 99/53979 A1 | 10/1999 |
| WO | WO 99/59658 A1 | 11/1999 |
| WO | WO 00/06227 A1 | 2/2000 |
| WO | WO 00/07539 A1 | 2/2000 |
| WO | WO 00/13723 A2 | 3/2000 |
| WO | WO 00/24441 A1 | 5/2000 |
| WO | WO 00/35516 | 6/2000 |
| WO | WO 00/50107 A1 | 8/2000 |
| WO | 00/61209 A1 | 10/2000 |
| WO | WO 00/61209 A1 | 10/2000 |
| WO | WO 00/64515 A1 | 11/2000 |
| WO | WO 00/69488 A2 | 11/2000 |
| WO | WO 01/05456 A1 | 1/2001 |
| WO | 01/49347 A1 | 7/2001 |
| WO | WO 01/49347 A1 | 7/2001 |
| WO | 01/60435 A1 | 8/2001 |
| WO | WO 01/60435 A1 | 8/2001 |
| WO | WO 01/76666 A1 | 10/2001 |
| WO | WO 01/77384 A2 | 10/2001 |
| WO | WO 01/87384 A1 | 11/2001 |
| WO | WO 02/11799 A1 | 2/2002 |
| WO | WO 02/47746 A1 | 6/2002 |
| WO | WO 02/056947 A1 | 7/2002 |
| WO | 02/074361 A2 | 9/2002 |
| WO | WO 02/074361 A2 | 9/2002 |
| WO | 03/015846 A2 | 2/2003 |
| WO | WO 03/013632 A2 | 2/2003 |

(56) References Cited

FOREIGN PATENT DOCUMENTS

| | | |
|---|---|---|
| WO | WO 03/015853 A1 | 2/2003 |
| WO | WO 03/039633 A2 | 5/2003 |
| WO | WO 03/041768 A | 5/2003 |
| WO | WO 03/047663 A2 | 6/2003 |
| WO | WO 03/051434 A2 | 6/2003 |
| WO | WO 03/066141 A1 | 8/2003 |
| WO | WO 03/092771 | 11/2003 |
| WO | WO 03/097133 | 11/2003 |
| WO | WO 03/099358 A2 | 12/2003 |
| WO | WO 2004/007554 A1 | 1/2004 |
| WO | WO 2004/011065 A1 | 2/2004 |
| WO | WO 2004/030732 A2 | 4/2004 |
| WO | WO 2004/035117 A2 | 4/2004 |
| WO | WO 2004/047890 A1 | 6/2004 |
| WO | WO 2004/047891 A1 | 6/2004 |
| WO | WO 2004/047892 A | 6/2004 |
| WO | WO 2004/054644 A1 | 7/2004 |
| WO | WO 2004/054645 A3 | 7/2004 |
| WO | WO 2004/087242 A1 | 10/2004 |
| WO | 2004/101025 A2 | 11/2004 |
| WO | WO 2004/101025 A2 | 11/2004 |
| WO | WO 2004/108194 A1 | 12/2004 |
| WO | 2005/004961 A1 | 1/2005 |
| WO | WO 2005/004961 A1 | 1/2005 |
| WO | WO 2005/009515 A1 | 2/2005 |
| WO | WO 2005/023341 A1 | 3/2005 |
| WO | WO 2005/025636 A2 | 3/2005 |
| WO | WO 2005/030301 A1 | 4/2005 |
| WO | WO 2005/035028 A1 | 4/2005 |
| WO | WO 2005/044345 A | 5/2005 |
| WO | WO 2005/044347 A1 | 5/2005 |
| WO | 2005/058393 A2 | 6/2005 |
| WO | WO 2005/058396 A1 | 6/2005 |
| WO | WO 2005/070481 A1 | 8/2005 |
| WO | WO 2005/082438 A1 | 9/2005 |
| WO | WO 2005/097238 A3 | 10/2005 |
| WO | 2005/105014 A2 | 11/2005 |
| WO | WO 2005/105014 A2 | 11/2005 |
| WO | 2005/115516 A1 | 12/2005 |
| WO | WO 2005/115507 A1 | 12/2005 |
| WO | WO 2005/115508 A1 | 12/2005 |
| WO | WO 2005/115509 A1 | 12/2005 |
| WO | WO 2005/115510 A1 | 12/2005 |
| WO | WO 2005/115512 A1 | 12/2005 |
| WO | WO 2005/115513 A1 | 12/2005 |
| WO | WO 2005/115514 A1 | 12/2005 |
| WO | WO 2005/115516 A1 | 12/2005 |
| WO | WO 2005/120607 A2 | 12/2005 |
| WO | 2006/008086 A1 | 1/2006 |
| WO | WO 2006/008086 A1 | 1/2006 |
| WO | WO 2006/044236 A2 | 4/2006 |
| WO | WO 2006/050304 A1 | 5/2006 |
| WO | WO 2006/062788 A2 | 6/2006 |
| WO | WO 2006/063015 A2 | 6/2006 |
| WO | WO 2006/063124 A2 | 6/2006 |
| WO | WO 2006/088513 A1 | 8/2006 |
| WO | WO 2006/088630 A2 | 8/2006 |
| WO | WO 2006/099441 A2 | 9/2006 |
| WO | 2006/106290 A1 | 10/2006 |
| WO | WO 2006/106290 A1 | 10/2006 |
| WO | WO 2006/106291 A1 | 10/2006 |
| WO | WO 2006/106292 A1 | 10/2006 |
| WO | WO 2006/106293 A1 | 10/2006 |
| WO | WO 2006/106294 A | 10/2006 |
| WO | WO 2006/106295 A1 | 10/2006 |
| WO | WO 2006/118616 A1 | 11/2006 |
| WO | WO 2006/129196 A1 | 12/2006 |
| WO | WO 2007/027204 A2 | 3/2007 |
| WO | WO 2007/036676 A1 | 4/2007 |
| WO | WO 2007/047200 A1 | 4/2007 |
| WO | WO 2007/051330 A1 | 5/2007 |
| WO | WO 2007/066152 A | 6/2007 |
| WO | 2007/129324 A2 | 11/2007 |
| WO | WO 2007/122193 A1 | 11/2007 |
| WO | WO 2007/131013 A | 11/2007 |
| WO | WO 2007/138299 A1 | 12/2007 |
| WO | WO 2008/047372 A2 | 4/2008 |
| WO | WO 2008/075033 A | 6/2008 |
| WO | WO 2008/093063 A2 | 8/2008 |
| WO | WO 88/08725 | 11/2008 |
| WO | 2010/023303 A1 | 3/2010 |

OTHER PUBLICATIONS

International Search Report dated Sep. 9, 2005; International Application No. PCT/GB2005/002120.
International Search Report dated Sep. 6, 2005; International Application No. PCT/GB2005/002108.
European Search Report dated Apr. 23, 2007; Application No. 06077332.2.
International Search Report dated Sep. 5, 2005; International Application No. PCT/GB2005/002105.
Singapore Search Report dated Feb. 26, 2008; Application No. 200608070-9.
International Search Report dated Sep. 5, 2005; International Application No. PCT/GB2005/002116.
International Search Report dated Sep. 5, 2005; International Application No. PCT/GB2005/002128.
Australian Search Report dated Dec. 11, 2007; Application No. 200608165-7.
International Search Report dated May 23, 2006; International Application No. PCT/GB2006/001017.
International Search Report dated May 29, 2006; International Application No. PCT/GB2006/001018.
International Search Report dated Jun. 2, 2006; International Application No. PCT/GB2006/001030.
International Search Report dated Jun. 1, 2006; International Application No. PCT/GB2006/001029.
International Search Report dated Sep. 9, 2005 International Application No. PCT/GB2005/002135.
International Search Report dated May 30, 2006; International Application No. PCT/GB2006/001031.
International Search Report dated Jun. 27, 2006; International Application No. PCT/GB2006/001023.
International Search Report dated Feb. 27, 2007; International Application No. PCT/1132006/002792.
European Search Report dated Feb. 1, 2006; Application No. 05255298.1.
Great Britain Search Report dated Sep. 22, 2006; Application No. GB0610860.9.
International Search Report dated Aug. 22, 2007; International Application No. PCT/GB2007/001992.
International Search Report dated Sep. 4, 2007; International Application No. PCT/GB2007/002002.
Great Britain Search Report dated Sep. 28, 2006; Application No. GB0610859.1.
International Search Report dated Aug. 22, 2007; International Application No. PCT/GB2007/001973.
International Search Report dated Feb. 26, 2008; International Application No. PCT/GB2007/004335.
International Search Report dated Sep. 13, 2007; International Application No. PCT/GB2007/001999.
International Search Report dated Aug. 28, 2007; International Application No. PCT/GB2007/001969.
International Search Report dated Oct. 10, 2008; International Application No. PCT/GB2008/002578.
Great Britain Search Report dated Nov. 12, 2007; Application No. GB0715460.2.
International Search Report dated Oct. 14, 2008; International Application No. PCT/GB2008/002580.
Great Britain Search Report dated Nov. 12, 2007; Application No. GB0715459.4.
International Search Report dated Nov. 27, 2008; International Application No. PCT/GB2008/002579.
Great Britain Search Report dated Nov. 12, 2007; Application No. GB0715461.0.
International Search Report dated Oct. 10, 2008; International Application No. PCT/GB2008/002573.

(56) References Cited

OTHER PUBLICATIONS

Great Britain Search Report dated Nov. 12, 2007; Application No. GB0715456.0.
International Search Report dated Oct. 10, 2008; International Application No. PCT/GB2008/002583.
Great Britain Search Report dated Nov. 12, 2007; Application No. GB0715457.8.
International Search Report dated Sep. 30, 2009; International Application No. PCT/GB2009/001447.
Great Britain Search Report dated Sep. 25, 2008; Application No. GB0811348.2.
International Search Report dated Oct. 2, 2009; International Application No. PCT/GB2009/001448.
Great Britain Search Report dated Sep. 25, 2008; Application No. GB0811346.6.
International Search Report dated Oct. 5, 2009; International Application No. PCT/GB2009/001451.
Great Britain Search Report dated Sep. 25, 2008; Application No. GB0811347.4.
International Search Report dated Oct. 6, 2009; International Application No. PCT/GB2009/001453.
Great Britain Search Report dated Sep. 25, 2008; Application No. GB0811345.8.
International Search Report dated Oct. 5, 2009; International Application No. PCT/GB2009/001445.
Great Britain Search Report dated Sep. 25, 2008; Application No. GB0811349.0.
International Search Report dated Jan. 22, 2010; International Application No. PCT/GB2009/001446.
Great Britain Search Report dated Sep. 25, 2008; Application No. GB0811343.3.
International Search Report dated Jan. 12, 2008; International Application No. PCT/GB2008/002475.
Great Britain Search Report dated Nov. 16, 2007; Application No. GB0716774.5.
European Search Report dated Aug. 3, 2011; Application No. 11170040.
European Search Report dated Aug. 3, 2011; Application No. 11163779.9.
Singapore Search Report dated Mar. 15, 2012; Application No. SG 201007017-5.
European Search Report dated Jul. 20, 2011; Application No. 11163762.5.
Australian Search Report dated Feb. 26, 2008; Application No. SG 200608071-7.
International Search Report dated Sep. 5, 2005; International Application No. PCT/GB2005/002137.
European Search Report dated Feb. 28, 2011; Application No. 10179733.0.
European Search Report dated Mar. 4, 2011; Application No. 10179736.3.
European Search Report dated Jun. 16, 2011; Application No. 11160134.0.
European Search Report dated Apr. 17, 2012; International Application No. 12157660.7.
European Search Report dated Apr. 17, 2012; International Application No. 12157661.5.
European Search Report Dated Oct. 16, 2012; International Application No. 12177505.0.
European Search Report dated Aug. 4, 2011; Application No. 11169691.0.
Great Britain Search Report dated Sep. 29, 2006; Application No. GB0610856.7.
Great Britain Search Report dated Sep. 19, 2006; Application No. GB0610861.7.
European Search Report dated Oct. 15, 2013; Application No. 12182553.3.
Great Britain Search Report dated Dec. 9, 2013; Application No. GB1310394.0.
International Search Report dated Sep. 8, 2014; International Application No. PCT/EP2014/062163.
Great Britain Search Report dated Dec. 8, 2013; Application No. GB1310389.0.
Great Britain Search Report dated Dec. 9, 2013; Application No. GB1310402.1.
International Search Report dated Sep. 17, 2014; International Application No. PCT/EP2014/062167.
Great Britain Search Report dated Dec. 9, 2013; Application No. GB1310392.4.
International Search Report dated Sep. 9, 2014; International Application No. PCT/EP2014/062168.
Great Britain Search Report dated Dec. 10, 2013; Application No. GB1310393.2.
International Search Report dated Sep. 8, 2014; International Application No. PCT/EP2014/062162.
Great Britain Search Report dated Dec. 10, 2013; Application No. GB1310372.6.
International Search Report dated Sep. 16, 2014; International Application No. PCT/EP2014/062160.
International Search Report dated Sep. 8, 2014; International Application No. PCT/EP2014/062166.
International Search Report dated Jan. 29, 2015; International Application No. PCT/EP2014/062167.

* cited by examiner

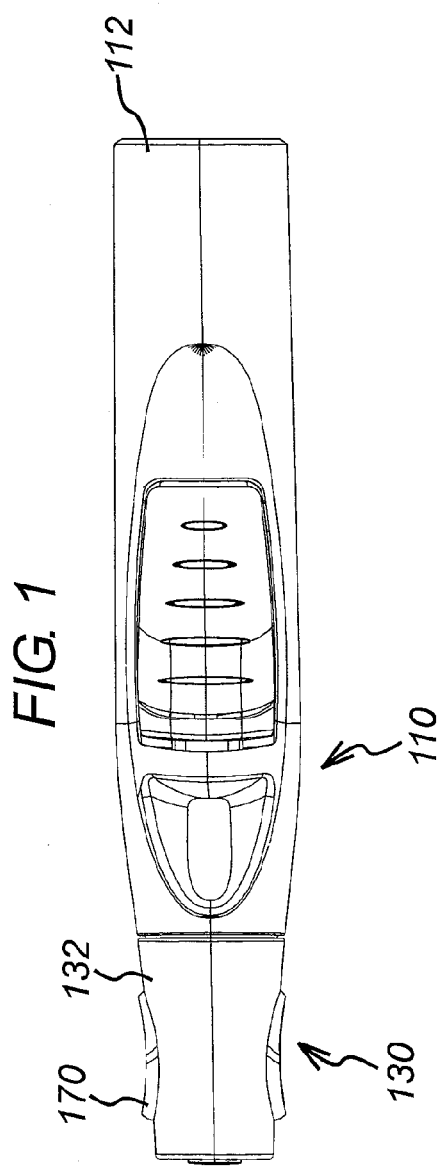
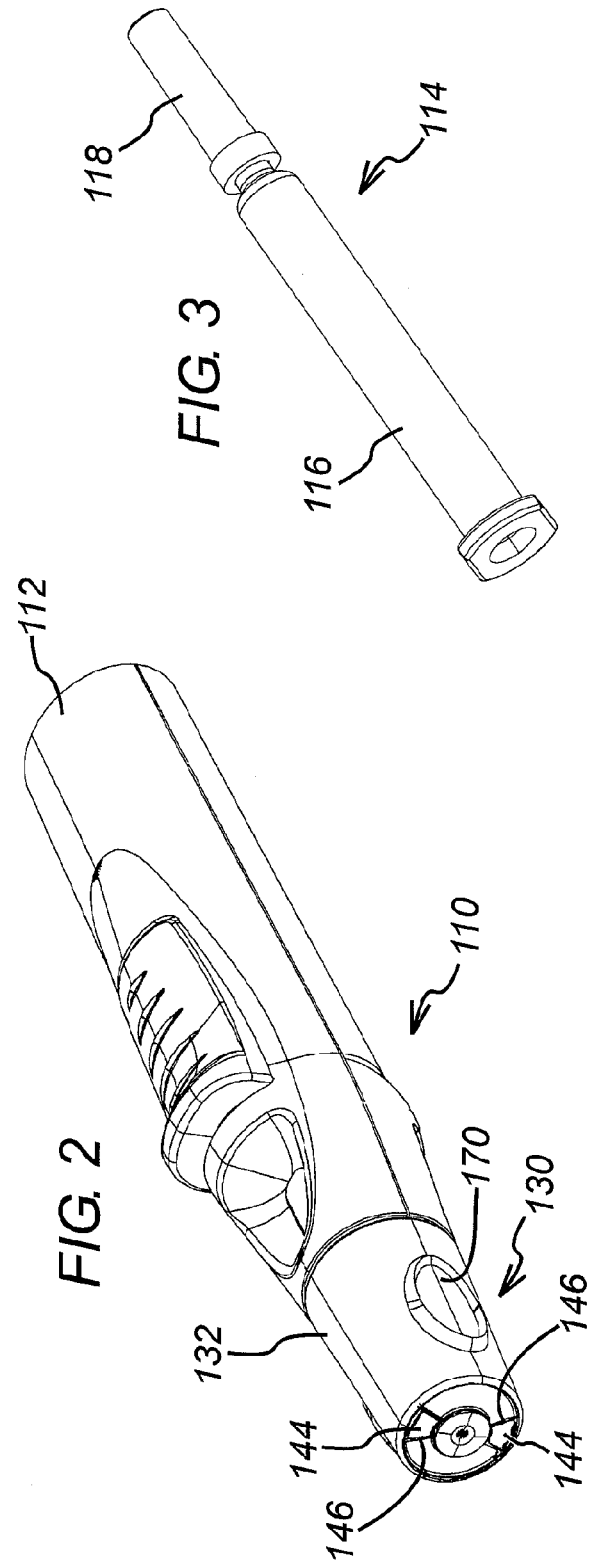

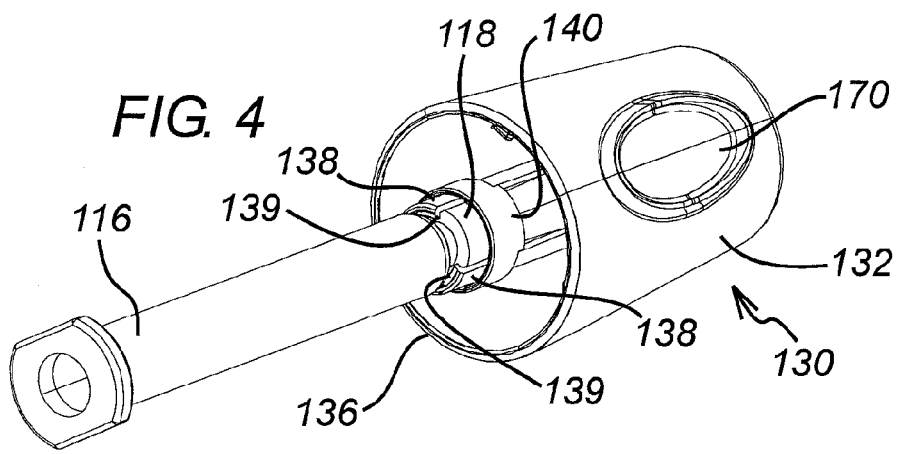
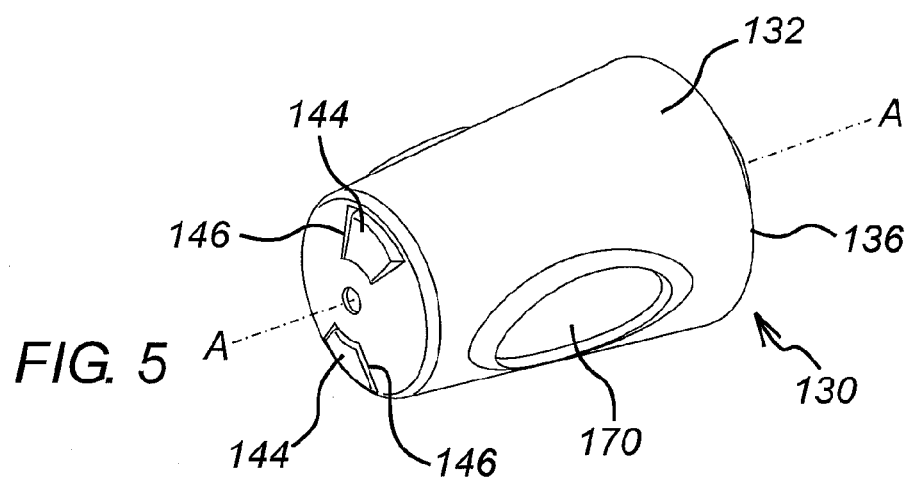
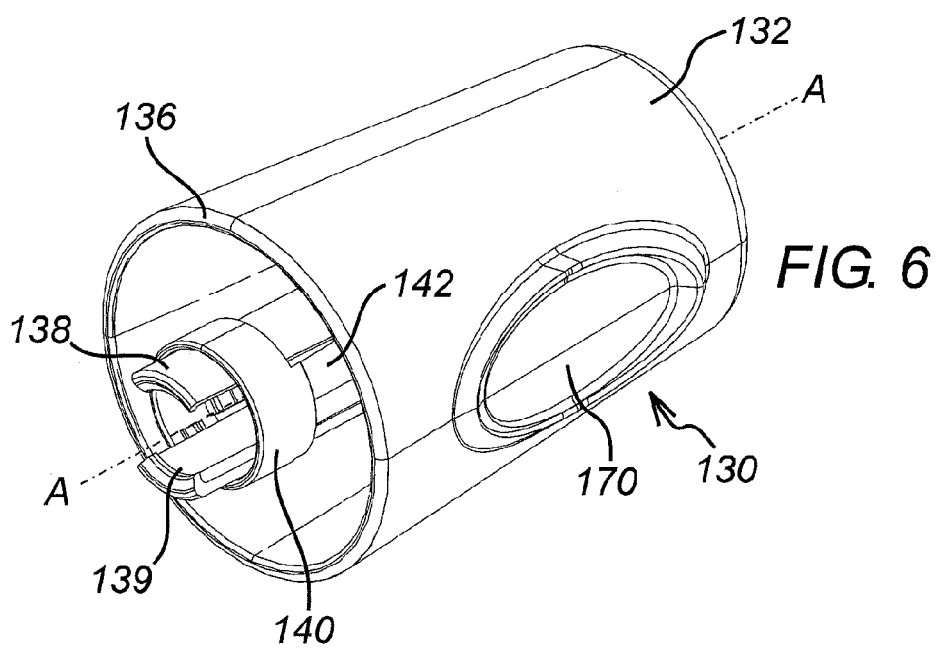

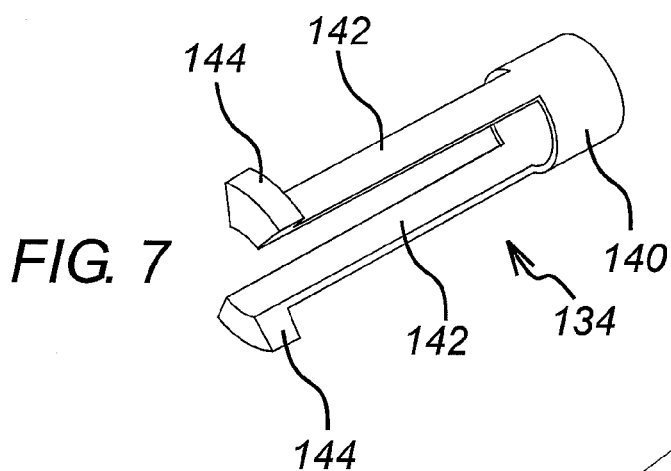
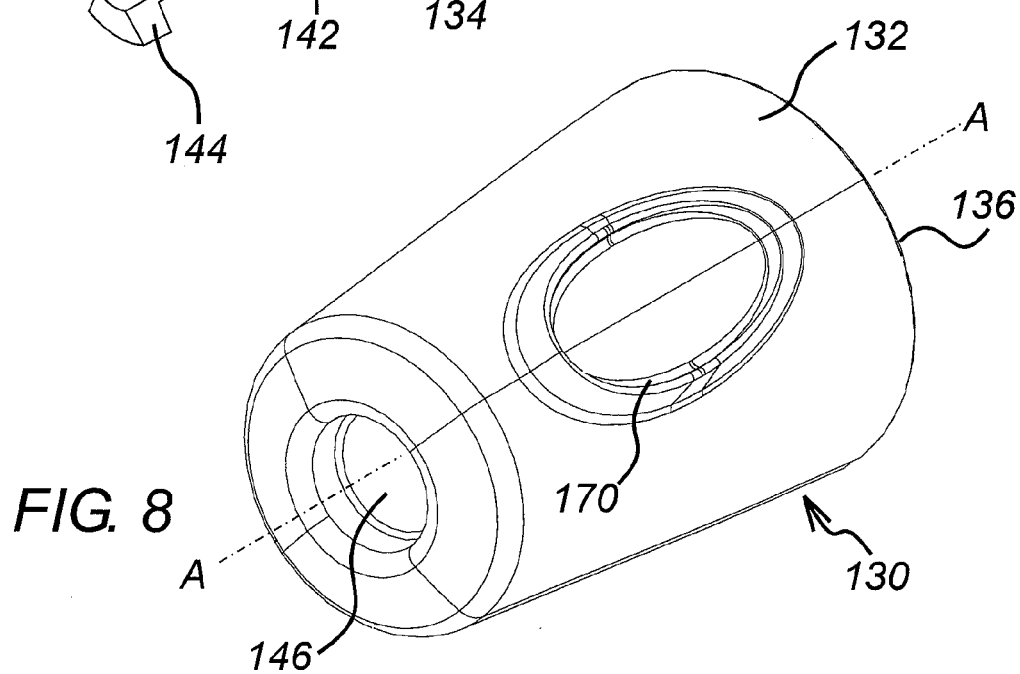
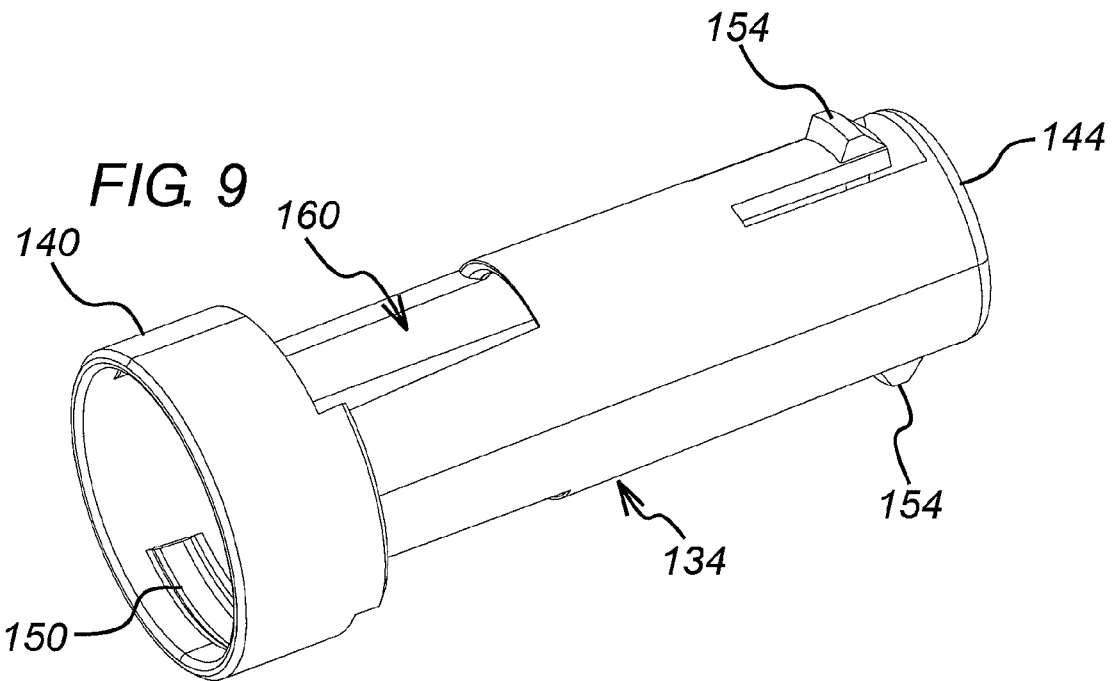

INJECTION DEVICE

BACKGROUND OF THE INVENTION

The present invention relates to an injection device of the type that receives a syringe, extends it, discharges its contents and then retracts it automatically.

BACKGROUND OF THE INVENTION

Devices of this general description are shown in WO 95/35126 and EP-A-0 516 473 and tend to employ a drive spring and some form of release mechanism that releases the syringe from the influence of the drive spring once its contents are supposed to have been discharged, to allow it to be retracted by a return spring.

Often, such injection devices are required to work with sealed hypodermic syringes which typically have a hermetically sealed cover or "boot" that covers the hypodermic needle and maintains the sterility of the syringe contents. The boot may be formed from a rubber material. Naturally, it is necessary to maintain the sterility of the syringe contents up to the point of administration, which means that the boot must be removed with the syringe inside the injection device.

Typically, the action required to remove the boot from the syringe entails either pulling the boot away from the syringe or twisting the boot and pulling it away from the syringe. If a filled syringe has been around for quite a while before it is used, it is often difficult to remove the boot from the syringe; a substantial force is often required.

The injection device may be designed so that removal of a cap of the injection device also removes the boot from the syringe. In such cases, the boot must be connected to the cap in such a way that the force required to remove the boot from the syringe is less than the force required to disconnect the boot from the cap. In order to connect the boot to the cap, an "insertion" force is exerted on the syringe. If this insertion force is too high, damage to the syringe and/or boot will occur, and the injection device will fail to operate correctly. The force required to remove a boot from a syringe is generally an order of magnitude greater than the maximum insertion force that can be exerted on the syringe via the boot without causing damage to the boot and/or syringe.

Therefore, there is a need for a means for connecting a cap of an injection device to a boot of a syringe in such a way that removal of the cap from the injection device causes removal of the boot from the syringe, and connection of the cap to the boot exerts a minimal force on the syringe and/or boot.

SUMMARY OF THE INVENTION

The methods and apparatus of the present invention are designed to address this need.

The present invention provides a cap for an injection device, the cap comprising:

a first part having a first end for receiving an injection device and a second end, the first part defining a first axis and having grip means for gripping the boot of a syringe, wherein the grip means is movable from a first position to a second position, the second position being further from the first axis than the first position; and a second part having retention means arranged such that movement of the retention means from a third position to a fourth position prevents the grip means from moving from the first position to the second position.

The first part may include a pair of arms, each arm having a first end and a second end, wherein the grip means is formed at a first end of each arm, the first ends of the arms being closer to the first end of the cap than the second ends of the arms. The grip means may comprise a hooked end portion. Each arm may be formed from a segment of a cylinder. When the grip means is in the first position, the first ends of the arms may be closer to the first axis than when the grip means is in the second position. The arms may be arranged so that the axis of the cylinder from which each arm is formed is substantially parallel to the first axis when the grip means is in the first position.

The movement of the retention means from the third position to the fourth position may be in a direction substantially parallel to the first axis. The retention means may comprise a ring shaped portion. The internal diameter of the ring shaped portion may be less than the distance between the first ends of the arms when the grip means is in the second position. When the retention means is positioned in the fourth position, the ring shaped portion may surround the first ends of the arms. Once the retention means has been moved from the third position to the fourth position, the retention means may prevent the grip means from moving from the first position to the second position. The ring shaped portion may have one of a groove and a ridge formed on an inner surface thereof. The arms of the first part may have the other of the groove and the ridge formed on an external surface and proximal to the first end thereof, such that when the retention means is positioned in the fourth position, the ridge on one of the first and second parts of the cap is positioned within the groove on the other of the first and second parts of the cap.

In a first embodiment, the second part may comprise a pair of legs, wherein a first end of each of the pair of legs is connected to the ring shaped portion. Each of the pair of legs may have a foot at a second end thereof. The second end of the first part of the cap may be provided with one or more apertures therethrough. When the retention means is in the third position, each leg may extend through one of the apertures. When the retention means is in the fourth position, each of the feet may be positioned within one of the apertures. The retention means may be moved from the third position to the fourth position by applying a force to the foot of each leg, thus forcing the legs through the apertures, the ring shaped portion from the third position to the fourth position and the grip means from the first position to the second position.

In a second embodiment, the second part may comprise a cylindrical member having the retention means at a first end thereof, and a foot at a second end thereof. The cylindrical member may be provided with a pair of opposing apertures through which the arms of the first part may extend. The second end of the first part of the cap may be provided with a central aperture therethrough. When the retention means is in the third position, the foot of the second part may protrude through the central aperture, and when the retention means is in the fourth position, the foot may be positioned within the first part of the cap or flush with the second end of the first part of the cap.

In either embodiment, the second part of the cap may further be provided with a movable protrusion which can communicate with a corresponding ridge proximal to the second end of the first part of the cap. The movable protrusion and the ridge function to maintain the second part in the third position until a force is applied to the foot or feet of the second part. The movable protrusion may be positioned proximal to the second end of the second part of the cap.

The cap may further comprise an external feature with which a user can grip the cap.

The present invention also provides an injection device comprising:

a housing containing a syringe having a discharge nozzle and a boot that covers its discharge nozzle, wherein the boot extends from a first end of the housing through an exit aperture; and a cap as recited above.

When the first part of the cap includes a pair of arms, each arm having a first end and a second end, and when the grip means is formed at a first end of each arm, the first ends of the arms being closer to the first end of the cap than the second ends of the arms, then the diameter of the boot may be more than the distance between the grip means at the first end of each arm when the grip means is in the first position so that movement of the grip means from the second position to the first position causes the cap to be connected to the boot, and removal of the cap from the housing when the grip means is in the second position causes removal of the boot from the syringe.

The force required to remove the boot from the syringe may be less than the force required to disconnect the boot from the cap when the grip means is in the first position and the retention means is in the fourth position.

The force required to disconnect the boot from the cap when the grip means is in the first position and the retention means is in the fourth position may be an order of magnitude greater than the force required to insert the boot into the cap when the grip means is in the first position and the retention means is in the third position.

The present invention also provides a method of attaching a cap to a boot of a syringe comprising:

providing a cap comprising:

a first part having a first end for receiving an injection device and a second end, the first part defining a first axis and having grip means for gripping the boot of a syringe, and a second part having retention means, wherein the grip means is arranged in a first position and the retention means is arranged in a third position;

inserting a boot of a syringe into the cap so that the grip means moves from the first position to a second position, the second position being further from the first axis than the first position, inserting the boot of the syringe further into the cap so that the grip means moves from the second position to the first position, and the boot is gripped by the grip means; and moving the retention means from the third position to a fourth position, thus preventing the grip means from moving from the first position to the second position, such that the boot cannot be removed from the cap.

When the first part includes a pair of arms, each arm having a first end and a second end, and the grip means is formed at a first end of each arm, the step of inserting the boot into the cap may comprise positioning the boot between the grip means at the first ends of each arm.

The first part and the grip means may be moulded as a single item.

BRIEF DESCRIPTION OF THE DRAWINGS

The invention will now be described by way of example with reference to the accompanying drawings, in which:

FIG. 1 shows a plan view of an injection device including a cap according to a first embodiment of the present invention;

FIG. 2 shows a perspective view of the injection device of FIG. 1;

FIG. 3 shows a perspective view of a syringe for use in an injection device according to the present invention;

FIG. 4 shows a perspective view of the syringe of FIG. 3 when connected to a cap according to a first or a second embodiment of the present invention;

FIG. 5 shows a perspective view from a first direction of a cap according to a first embodiment of the present invention;

FIG. 6 shows a perspective view from a second direction of a cap according to a first or a second embodiment of the present invention;

FIG. 7 shows a perspective view of a second part of a cap according to a first embodiment of the present invention.

FIG. 8 shows a perspective view from a first direction of a cap according to a second embodiment of the present invention;

FIG. 9 shows a perspective view of a second part of a cap according to a second embodiment of the present invention;

DETAILED DESCRIPTION OF THE INVENTION

Figure 10A:
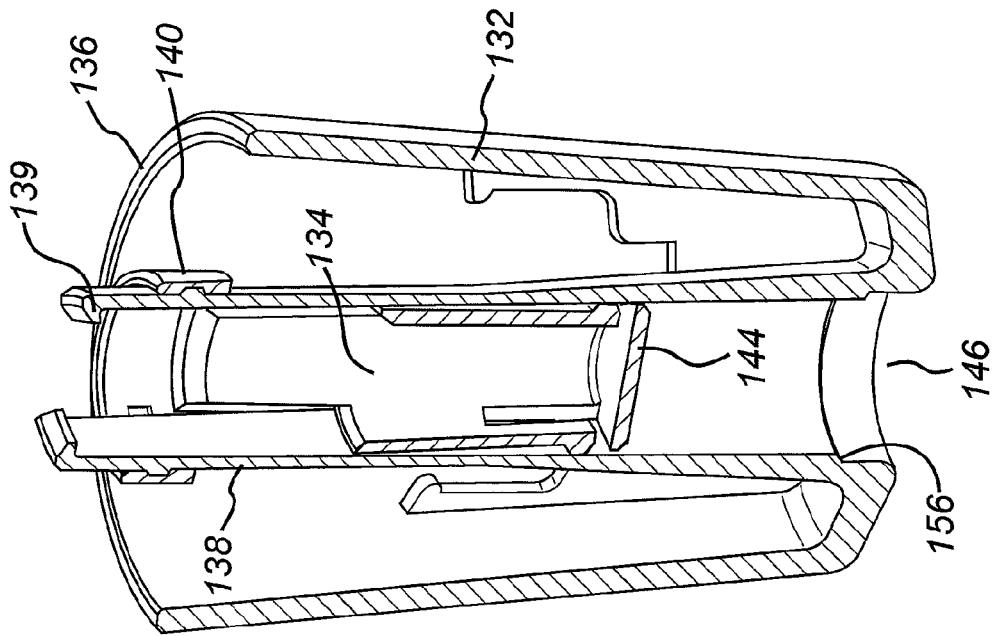
FIGS. 10a and 10b show cut-away views of a cap according to a second embodiment of the present invention with the second part of the cap positioned in third and fourth positions respectively.

FIG. 1 shows an injection device 110 according to the present invention. The injection device has an injection device housing 112.

The housing 112 contains a hypodermic syringe 114 of conventional type as shown in FIG. 3. The syringe includes a syringe body 116 defining a reservoir and terminating at one end in a hypodermic needle. The syringe 114 has a hermetically sealed cover or "boot" 118 that covers the hypodermic needle and maintains the sterility of the syringe contents. The boot is generally formed of a soft rubber or plastics material. Whilst the syringe illustrated is of hypodermic type, this need not necessarily be so. Transcutaneous or ballistic dermal and subcutaneous syringes may also be used with the injection device of the present invention.

The injection device is further provided with a cap 130. The cap comprises a first part 132 and a second part 134.

According to a first embodiment of the invention, as shown in FIGS. 1, 2 and 4 to 7, the first part 132 has a first end 136 for attachment to the housing 112 of the injection device 110. The first part 132 also includes grip means 139 for gripping the boot 118 of the syringe 114. The first part 132 includes a pair of arms 138, each having a first end and a second end. The grip means 139 are formed at the first end of each arm 138. Each arm 138 is formed from the segment of a cylinder. The arms 138 and grip means 139 are movable from a first position to a second position wherein the second position is further away than the first position from a first axis A-A defined by the first part 132 of the cap 130.

The second part 134 includes retention means for retaining the grip means 139 in the first position. The retention means comprises a ring-shaped portion 140. The internal diameter of the ring shaped portion 140 is less than the distance between the first ends of the arms 138 when the arms 138 are in the second position. The retention means is movable in a direction parallel to the axis A-A from a third position to a fourth position. When the retention means is in the third position, the ring shaped portion 140 surrounds the second end of the arms 138. When the retention means is in the fourth position, as shown in FIGS. 1 to 6, the ring shaped portion 140 is proximal to the grip means 139 and prevents the arms 138 from moving into the second position.

The second part 134 also includes a pair of legs 142. A first end of each leg 142 is connected to the ring shaped portion 140. Each leg has a foot 144 at a second end thereof.

The second end of the first part 132 of the cap 130 is provided with a pair of apertures 146. When the retention means is in the fourth position, as shown in FIGS. 1 to 6, the feet 144 are positioned within the apertures 146. When the retention means is in the third position, the legs 142 extend through the apertures 146 and the ring shaped portion 140 is close to the second end of the first part 132 of the cap. In order to move the second part 134 from the third position to the fourth position, a force is applied to each foot 144. The legs move through the apertures 146 until the feet are positioned within the apertures 146. With this movement, the ring shaped portion 140 slides along the arms 138 until it is proximal to the first end of the arms 138, thus preventing the arms 138 from moving from the first position, away from the axis A-A, towards the second position.

During manufacture of the injection device 110, the syringe 114 and boot 118 are inserted into the housing as a single piece. In order to attach the cap 130 to the boot 118, the cap 130 is provided with the arms 138 in the first position and the ring shaped portion 140 in the third position, such that the legs 142 extend through the apertures 146. The cap 130 is then placed on the housing 110. As the cap 130 is pushed onto the housing, the boot 118 forces the arms 138 from the first position to the second position until the grip means reach the end of the boot 118 at which point the arms 138 spring from the second position to the first position. Consequently, the boot ends up positioned between the legs 138 of the first part 132. A force is then applied to the feet 144, which, in turn, pushes the ring shaped portion 140 down the outside of the arms 138, until the ring shaped portion is proximal to the first end of the arms 138, thus preventing the arms 138 from moving from the first position, away from the axis A-A, towards the second position.

According to a second embodiment of the invention, as shown in FIGS. 1, 4, 6 and 8 to 10, the first part 132 has a first end 136 for attachment to the housing 112 of the injection device 110. The first part 132 also includes grip means 139 for gripping the boot 118 of the syringe 114. The first part 132 includes a pair of arms 138, each having a first end and a second end. The grip means 139 are formed at the first end of each arm 138. Each arm 138 is formed from the segment of a cylinder. The arms 138 and grip means 139 are movable from a first position to a second position wherein the second position is further away than the first position from a first axis A-A defined by the first part 132 of the cap 130.

Figure 10B:
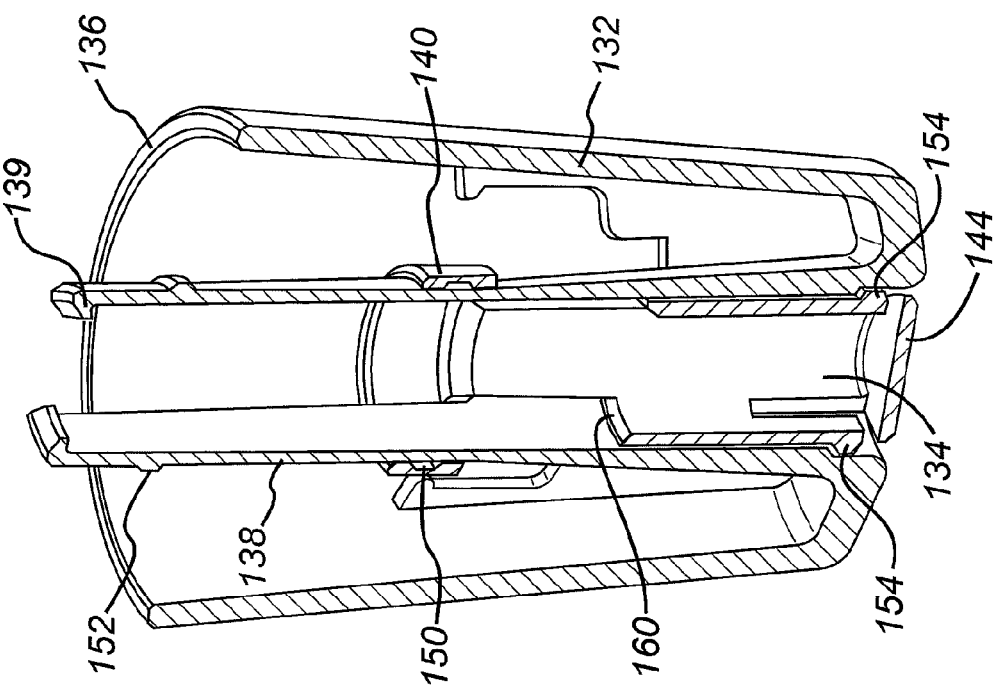

The second part 134 includes retention means for retaining the grip means 139 in the first position. The retention means comprises a ring-shaped portion 140. The internal diameter of the ring shaped portion 140 is less than the distance between the first ends of the arms 138 when the arms 138 are in the second position. The retention means is movable in a direction parallel to the axis A-A from a third position, as shown in FIG. 10*a*, to a fourth position, as shown in FIG. 10*b*. When the retention means is in the third position, as shown in FIG. 10*a*, the ring shaped portion 140 surrounds a central portion of the arms 138. When the retention means is in the fourth position, as shown in FIG. 10*b*, the ring shaped portion 140 is proximal to the grip means 139 and prevents the arms 138 from moving into the second position.

The ring shaped portion 140 has a groove 150 formed on its inner surface. The arms 138 of the first part 132 have a corresponding ridge 152 formed on an external surface, proximal to the first end of the arms 138. When the retention means is positioned in the fourth position, as shown in FIG. 10*b*, the ridge 152 on the arms 138 is positioned within the groove 150 on the ring shaped portion 140.

The second part 134 comprises a cylindrical member with the retention means at a first end thereof, and a foot 144 at a second end thereof. The cylindrical member is provided with a pair of opposing apertures 160 through which the arms 138 of the first part extend.

The second end of the first part 132 of the cap 130 is provided with a central aperture 146. When the retention means is in the third position, as shown in FIG. 10*a*, the foot 144 of the second part 134 protrudes through the central aperture 146. When the retention means is in the fourth position, as shown in FIG. 10*b*, the foot 144 is positioned within the first part of the cap.

The second part 134 of the cap is further provided with a movable protrusion 154 which can communicate with a corresponding ridge 156 proximal to the second end of the first part 132 of the cap. The movable protrusion 154 and the ridge 156 function to maintain the second part 134 in the third position until a force is applied to the foot 144 of the second part 134.

In order to move the second part 134 from the third position to the fourth position, a force is applied to the foot 144. The movable protrusions 154 move towards the axis A-A and ride over the ridge 156. The apertures 160 move over the arms 138 until the groove 150 on the ring-shaped portion 140 engages the ridge 152 on the arms 138 and the foot 144 is positioned within the first part 132 of the cap. With this movement, the ring shaped portion 140 slides along the arms 138 until it is proximal to the first end of the arms 138, thus preventing the arms 138 from moving from the first position, away from the axis A-A, towards the second position.

During manufacture of the injection device 110, the syringe 114 and boot 118 are inserted into the housing as a single piece. In order to attach the cap 130 to the boot 118, the cap 130 is provided with the arms 138 in the first position and the ring shaped portion 140 in the third position, such that the foot 144 protrudes from the aperture 146. The cap 130 is then placed on the housing 110. As the cap 130 is pushed onto the housing, the boot 118 forces the arms 138 from the first position to the second position until the grip means reach the end of the boot 118 at which point the arms 138 spring from the second position to the first position. Consequently, the boot 118 ends up positioned between the legs 138 of the first part 132. A force is then applied to the foot 144, which, in turn, pushes the ring shaped portion 140 down the outside of the arms 138, until the groove 150 and ridge 152 engage and the ring shaped portion 140 is proximal to the first end of the arms 138, thus preventing the arms 138 from moving from the first position, away from the axis A-A, towards the second position.

In both embodiments, when the injection device 110 is to be used, the user holds the housing 112 with one hand, and grips the cap 130 with the other hand using the grip surfaces 170. The user then pulls the cap 130 away from the housing 112. The grip means 139 grip the boot 118 and, in pulling the cap 130 away from the housing 110, the boot 118 is also removed from the syringe 114.

The force required to remove the boot 118 from the syringe 114 is significantly less than the force required to disconnect the boot 118 from the cap 130 when the grip means is gripping the boot 118.

The force required to disconnect the boot 118 from the cap 130 when the grip means is gripping the boot is significantly greater than the force required to insert the boot 118 into the cap 130 when the retention means is in the third position. For example, the force required to insert the boot between the arms 138 when the retention means is in the first position is less than 1N, whereas the force required to remove the cap 130 from the boot 118 when the retention means is in the fourth position is of the order of 60N.

The exterior of the cap 130 is provided with a pair of grip surfaces 170. These grip surfaces 170 provide a surface through which the user can grip the cap 130.

The present invention provides a simple and effective way of solving the problems of the prior art devices. Since no modifications need to be made to the syringe or boot, a standard syringe can be used, and manufacturing costs can be reduced.

It will of course be understood that the present invention has been described by way of example, and that modifications of detail can be made within the scope of the invention as defined by the following claims.

The invention claimed is:

1. A cap for an injection device, the cap comprising:
   a first part having a first end for receiving an injection device and a second end, the first part defining a first axis and having grip means for gripping a boot of a syringe, wherein the grip means is movable by a force from a first position to a second position and the grip means is capable of springing back from the second position to the first position, the second position being further from the first axis than the first position; and
   a second part having retention means for retaining the grip means, the retention means arranged such that movement of the retention means from a third position to a fourth position prevents the grip means from moving from the first position to the second position.

2. A cap according to claim 1, wherein the first part includes a pair of arms, each arm having a first end and a second end, wherein the grip means is formed at a first end of each arm, and the first ends of the pair of arms are closer to the first end of the first part than the second ends of the pair of arms.

3. A cap according to claim 2, wherein the grip means comprises a hooked end portion.

4. A cap according to claim 2, wherein each arm is formed from a segment of a cylinder.

5. A cap according to claim 4, wherein the pair of arms are arranged so that an axis of the cylinder from which each arm is formed is substantially parallel to the first axis when the grip means is in the first position.

6. A cap according to claim 2 wherein, when the grip means is in the first position, the first ends of the pair of arms are closer to the first axis than when the grip means is in the second position.

7. A cap according to claim 2 wherein the retention means comprises a ring shaped portion.

8. A cap according to claim 2 wherein the retention means comprises a ring shaped portion having an internal diameter which is less than a distance between the first ends of the pair of arms when the grip means is in the second position.

9. A cap according to claim 8 wherein when the retention means is positioned in the fourth position, the ring shaped portion surrounds the first ends of the pair of arms.

10. A cap according to claim 7, wherein the ring shaped portion includes one of a groove and a ridge formed on an inner surface thereof.

11. A cap according to claim 10, wherein the pair of arms of the first part have the other of the groove and the ridge formed on an external surface and proximal to the first end thereof.

12. A cap according to claim 7 wherein the second part further includes a pair of legs, wherein a first end of each of the pair of legs is connected to the ring shaped portion.

13. A cap according to claim 12 wherein each of the pair of legs has a foot at a second end thereof.

14. A cap according to claim 12 wherein the second end of the first part of the cap is provided with one or more apertures therethrough.

15. A cap according to claim 14, wherein when the retention means is in the third position, each leg extends through one of the apertures.

16. A cap according to claim 14 wherein when the retention means is in the fourth position, each of the feet is positioned within one of the apertures.

17. A cap according to claim 13, wherein the retention means can be moved from the third position to the fourth position by applying a force to the foot of each leg.

18. A cap according to claim 7 wherein the second part comprises a cylindrical member having the retention means at a first end thereof, and a foot at a second end thereof.

19. A cap according to claim 18 wherein the cylindrical member has a pair of opposing apertures therethrough, through which the pair of arms of the first part extend.

20. A cap according to claim 18 wherein the second end of the first part of the cap is provided with a central aperture therethrough.

21. A cap according to claim 20 wherein when the retention means is in the third position, the foot of the second part protrudes through the central aperture, and when the retention means is in the fourth position, the foot is positioned within the first part of the cap or flush with the second end of the first part of the cap.

22. A cap according to claim 1 wherein the second part of the cap is provided with a movable protrusion which can communicate with a corresponding ridge proximal to the second end of the first part of the cap.

23. An injection device comprising:
   a housing containing a syringe having a discharge nozzle and a boot that covers the discharge nozzle, wherein the boot extends from a first end of the housing through an exit aperture; and
   a cap according to claim 1.

24. An injection device according to claim 23, including a cap wherein the first part includes a pair of arms, each arm having a first end and a second end, wherein the grip means is formed at a first end of each arm, and the first ends of the pair of arms are closer to the first end of the first part than the second ends of the pair of arms, and wherein a diameter of the boot is more than a distance between the grip means at the first end of each arm when the grip means is in the first position.

25. A method of attaching a cap to a boot of a syringe comprising:
   providing a cap comprising:
      a first part having a first end for receiving an injection device and a second end, the first part defining a first axis and having grip means for gripping the boot of a syringe, and
      a second part having retention means for retaining the grip means, wherein
      the grip means is arranged in a first position and the retention means is arranged in a third position;
   inserting a boot of a syringe into the cap so that the grip means moves from the first position to a second position, the second position being further from the first axis than the first position,
   inserting the boot of the syringe further into the cap so that the grip means moves from the second position to the first position, and the boot is gripped by the grip means; and moving the retention means from the third position to a fourth position, thus preventing the grip means from moving from the first position to the second position, such that the boot cannot be removed from the cap.

26. The method of claim 25, wherein the first part includes a pair of arms, each arm having a first end and a second end, and the grip means is formed at a first end of each arm, and the step of inserting the boot into the cap comprises positioning the boot between the grip means at the first ends of each arm.

\* \* \* \* \*